(12) United States Patent
Isobe et al.

(10) Patent No.: US 8,580,234 B2
(45) Date of Patent: Nov. 12, 2013

(54) METHOD FOR REMOVING SOLID PRODUCT FORMED ON SURFACES OF TEETH

(75) Inventors: Tsutomu Isobe, Sumida-ku (JP);
Yoshiyuki Eshita, Sumida-ku (JP);
Kazuhiko Kato, Sumida-ku (JP);
Masanobu Wakasa, Wakayama (JP);
Kenji Manago, Wakayama (JP);
Kuniyuki Nakanishi, Wakayama (JP);
Noriyuki Tanji, Wakayama (JP)

(73) Assignee: Kao Corporation, Tokyo (JP)

( * ) Notice: Subject to any disclaimer, the term of this patent is extended or adjusted under 35 U.S.C. 154(b) by 219 days.

(21) Appl. No.: 13/129,291

(22) PCT Filed: Oct. 23, 2009

(86) PCT No.: PCT/JP2009/005592
§ 371 (c)(1),
(2), (4) Date: May 13, 2011

(87) PCT Pub. No.: WO2010/058522
PCT Pub. Date: May 27, 2010

(65) Prior Publication Data
US 2011/0223119 A1    Sep. 15, 2011

(30) Foreign Application Priority Data

| Nov. 19, 2008 | (JP) | 2008-296086 |
| Nov. 19, 2008 | (JP) | 2008-296104 |
| Jan. 26, 2009 | (JP) | 2009-014807 |

(51) Int. Cl.
*A61K 8/55* (2006.01)
*A61Q 11/00* (2006.01)

(52) U.S. Cl.
USPC ............................. 424/57; 424/52

(58) Field of Classification Search
USPC .................................... 424/49–58
See application file for complete search history.

(56) References Cited

U.S. PATENT DOCUMENTS

| 4,826,675 | A * | 5/1989 | Gaffar et al. ............. 424/52 |
| 5,059,417 | A   | 10/1991 | Williams et al. |
| 2004/0126335 | A1 | 7/2004 | Fuller et al. |
| 2006/0147392 | A1 * | 7/2006 | Ono et al. ............. 424/49 |
| 2007/0122357 | A1 | 5/2007 | Glandorf |
| 2007/0183991 | A1 * | 8/2007 | Katou et al. .......... 424/58 |

FOREIGN PATENT DOCUMENTS

| CN | 1247057 A | 3/2000 |
| CN | 1593376 A | 3/2005 |
| JP | A-52-108029 | 9/1977 |
| JP | A-56-018911 | 2/1981 |
| JP | A-56-18913 | 2/1981 |
| JP | B-61-23768 | 6/1986 |
| JP | A-62-198611 | 9/1987 |
| JP | A-1-104004 | 4/1989 |
| JP | A-1-203316 | 8/1989 |
| JP | A-1-305020 | 12/1989 |
| JP | B-6-8248 | 2/1994 |
| JP | A-7-285839 | 10/1995 |
| JP | A-8-319224 | 12/1996 |
| JP | A-9-202718 | 8/1997 |
| JP | A-10-017447 | 1/1998 |
| JP | A-10-87458 | 4/1998 |
| JP | A-10-182383 | 7/1998 |
| JP | A-10-298049 | 11/1998 |
| JP | A-11-116421 | 4/1999 |
| JP | A-11-349460 | 12/1999 |
| JP | A-2000-26259 | 1/2000 |
| JP | A-2003-335646 | 11/2003 |
| JP | A-2005-008579 | 1/2005 |
| JP | A-2007-153841 | 6/2007 |
| JP | A-2008-013528 | 1/2008 |
| JP | A-2009-263268 | 11/2009 |
| JP | A-2009-263281 | 11/2009 |
| WO | WO 2007/063506 A2 | 6/2007 |
| WO | WO 2007/111616 A1 | 10/2007 |

OTHER PUBLICATIONS

JP56-018913 Tsutsui et al English translation (Feb. 1981).*
"Notification of First Office Action" for Chinese patent application No. 200980146328.1, mailed Aug. 10, 2012, Patent Office of the People's Republic of China, Beijing, China.
International Search Report (ISR) for PCT/JP2009/005592, I.A. fd: Oct. 23, 2009, mailed Dec. 28, 2009 from Japanese Patent Office, Tokyo, Japan.
International Preliminary Report on Patentability (IPRP), Chapter I of the Patent Cooperation Treaty, including the Written Opinion for PCT/JP2009/005592, I.A. fd: Oct. 23, 2009, issued Jun. 21, 2011 from the International Bureau of WIPO, Geneva, Switzerland.

* cited by examiner

*Primary Examiner* — Walter Webb
(74) *Attorney, Agent, or Firm* — Sterne, Kessler, Goldstein & Fox P.L.L.C.

(57) ABSTRACT

The invention provides a composition capable of exerting an excellent whitening effect and imparting gloss to teeth.
A method for removing a solid product formed on surfaces of teeth, the method containing applying an oral composition to teeth, wherein the oral composition contains 0.05 to 18% by weight of phytic acid or a salt thereof, and contains no polyvalent cation or contains a polyvalent cation in an amount of less than 0.1 fold mol relative to phytic acid, and wherein the oral composition, as diluted with water to 30% by weight, has a pH of 5.5 to 6.5.

9 Claims, 2 Drawing Sheets

(a)  (b)

(c)  (d)

(a)  (b)

White tooth (Tooth A) — Vacancy is present in interprismatic space (a)

Stained tooth (Tooth B) — Interprismatic space is not clear (filled) (b)

(a) Tooth B after immersion (b) Tooth B before immersion

METHOD FOR REMOVING SOLID PRODUCT FORMED ON SURFACES OF TEETH

FIELD OF THE INVENTION

The present invention relates to a method for removing a solid product formed on surfaces of teeth to improve the gloss of the teeth.

BACKGROUND OF THE INVENTION

Staining of human teeth is caused mainly by calculus or plaque, or by adhesion of various staining substances on surfaces. Various physical or chemical methods have been presented as means of eliminating the cause of staining tooth surfaces. In addition to removal by polishing, physical methods include a method for removing staining substances by use of n-butyl ether, butyl butyrate, or the like (Patent Document 1, Patent Document 2), and a method for improving a color tone by covering a tooth by use of a ceramic veneer, etc. Known chemical methods include a method for promoting remineralization by an oral composition containing hydroxyapatite (Patent Document 3, Patent Document 4), a method for bleaching oxidatively by use of a peroxide (Patent Document 5), a method using a tooth whitening composition containing a peroxide as well as a self-curing calcium phosphate compound and a fluorine compound or the like (Patent Document 6), a method for promoting enamel remineralization by use of an oral composition containing a liquefied calcium phosphate compound (Patent Document 7), etc. Further, an oral composition using a combination of a polyvalent metal cation and polyphosphoric acid to prevent calculus and staining (Patent Document 8) is also known.

However, in case of the method using a ceramic veneer, etc., reduction of tooth mass is required, and for the use of the method a guidance or treatment by a dentist is required. Further, the method for bleaching oxidatively by use of a peroxide needs to use a high concentration of peroxide to allow teeth to be bleached oxidatively, and therefore it must be carried out cautiously under a guidance of a specialist. According to this method, although teeth can be whitened, the gloss is deteriorated. Furthermore, even under a guidance of a specialist, there are risks that the peroxide may damage teeth or gingiva, and cause hypersensitivity.

Meanwhile, the method for promoting remineralization of teeth by use of a calcium phosphate compound such as hydroxyapatite is mainly to repair enamel surfaces with apatite to thereby restore the tooth health, and is not satisfactory in terms of whitening effect. Further, in case of the combined use of polyphosphoric acid and a polyvalent metal cation, the whitening effect is not adequate again. None of such conventional whitening dentifrices can impart gloss to teeth, especially gloss to teeth themselves.

It has been known that phytic acid has activities, such as removal of tobacco tar, suppressive effect against calculus, and stabilization of stannous fluoride, and a cleansing agent and a dentifrice, each containing phytic acid have been reported (Patent Document 9), Further, to improve astringency in intraoral application of a composition containing phytic acid, known are various techniques of mixing phytic acid with an amphoteric electrolyte, such as an amino acid and a protein (Patent Document 10), a specific flavor component (Patent Document 11), a chain hydrocarbon compound (Patent Document 12), polyvinyl alcohol or polyvinylpyrrolidone (Patent Document 13), or the like. Further, to improve the astringency of a polyphosphate, a technique of mixing an alkali metal sulfate therewith is known (Patent Document 14).

PRIOR ART DOCUMENTS

Patent Document

Patent Document 1: JP-A-1-203316
Patent Document 2: JP-A-1-104004
Patent Document 3: JP-A-1-305020
Patent Document 4: JP-A-9-202718
Patent Document 5: JP-B-6-8248
Patent Document 6: JP-A-11-116421
Patent Document 7: JP-A-8-319224
Patent Document 8: JP-A-52-108029
Patent Document 9: JP-A-56-18913
Patent Document 10: JP-B-61-23768
Patent Document 11: JP-A-62-198611
Patent Document 12: JP-A-10-87458
Patent Document 13: JP-A-2000-26259
Patent Document 14: JP-A-7-285839

SUMMARY OF THE INVENTION

Problem to be Solved by the Invention

The present invention provides a method which is capable of having an excellent whitening effect on teeth as well as imparting gloss to teeth.

Means for Solving the Problem

Under such circumstances, the present inventors have studied a relationship between the surface condition of teeth and the whiteness and gloss (luster) of the teeth using scanning electron microscope and found that most of staining substances formed on the tooth surfaces can be removed, for example, by toothbrushing with a abrasive, but that small solid products with a height (thickness or diameter) of less than 1 μm cannot be removed properly with a conventional whitening agent or abrasive. As a result of further studies, it has been found that the presence or absence of such a small solid product affects substantially the gloss of teeth, that the small solid product can be removed by a composition which has a certain range of pH, does not contain a polyvalent cation, and contains phytic acid, and that both whitening and imparting gloss to teeth can be accomplished simultaneously by use of the composition.

Further, the present inventors have found that addition of erythritol in a certain amount or more to the composition containing phytic acid provides an oral composition improving remarkably a frictional feel of teeth caused by phytic acid and presenting a fresh and good sense of use in addition to the aforementioned removing effect on the solid product formed on surfaces of teeth.

In other words, the present invention provides a method for removing a solid product formed on surfaces of teeth, which contains applying an oral composition to teeth, wherein the oral composition contains 0.05 to 18% by weight of phytic acid or a salt thereof, and contains no polyvalent cation or contains a polyvalent cation, in an amount of less than 0.1-fold mol relative to the phytic acid, and wherein the oral composition, as diluted with water to 30% by weight, has a pH of 5.5 to 6.5.

Further, the present invention provides a use of an oral composition for removing a solid product formed on surfaces of teeth, wherein the oral composition contains 0.05 to 5% by weight of phytic acid or a salt thereof, and does not contain a polyvalent cation or contains a polyvalent cation in an amount of less than 0.1-fold mol relative to the phytic acid, and wherein the oral composition, as diluted with water to 30% by weight, has a pH of 5.5 to 6.5.

Further, the present invention provides a method for imparting gloss to teeth by removing a sold product formed on surfaces of teeth, which contains applying an oral composition to teeth, wherein, the oral composition contains 0.05 to 18% by weight of phytic acid or a salt thereof, and contains no polyvalent cation or contains a polyvalent cation in an amount of less than 0.1-fold mol relative to the phytic acid, and wherein the oral composition, as diluted with water to 30% by weight, has a pH of 5.5 to 6.5.

Further, the present invention provides an oral composition containing the following components (A) and (B):
(A) phytic acid or a salt thereof in an amount of 0.01 to 10% by weight, and
(B) erythritol in an amount of 3 to 60% by weight; wherein the weight ratio (B/A) of the component (B) to the component (A) is 5 to 1000.

Note that the water is purified water, and represents ion exchanged water or distilled water.

Advantageous Effects of the Invention

According to the present invention, a small solid product with the thickness of less than 1 μm deposited on surfaces of teeth, which could not be removed by using a conventional dentifrice, can be removed to make teeth white and impart gloss to teeth.

Further, by use of an oral composition containing erythritol in a certain amount or more to phytic acid, the small solid product on tooth surfaces can be removed, a frictional feel of teeth characteristic of phytic acid can be improved and a fresh sense of use can be obtained. Here, a frictional feel of teeth means a feel sensed when teeth are contacted or rubbed with each other, which is a physical discomfort. The present invention can provide an oral composition, which offers a good sense of use felt by teeth as well as an improved texture of tooth surfaces.

EMBODIMENTS FOR CARRYING OUT THE INVENTION

Figure 1:
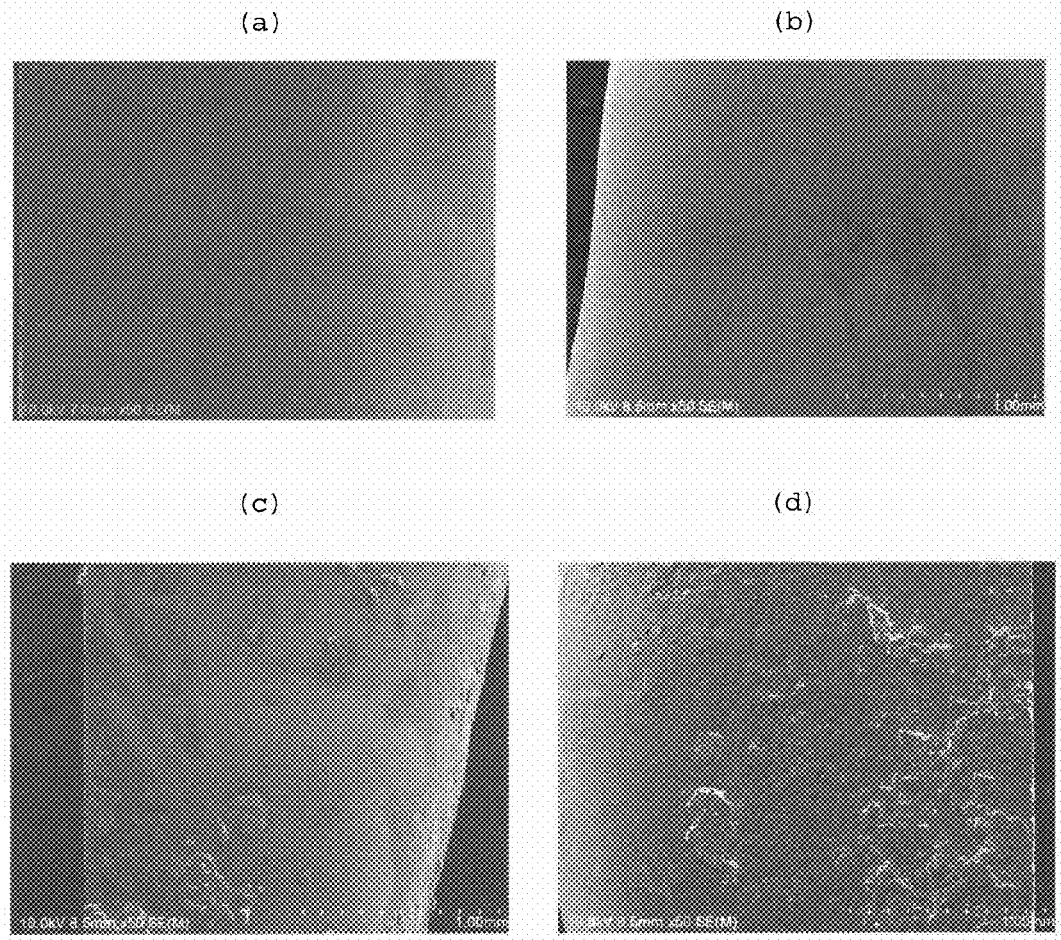
FIG. 1 is photographs of a tooth surface before and after a brushing treatment, observed with electron microscope (magnification ×50).

An active ingredient of an oral composition used in the method for removing a small solid product with a thickness of less than 1 μm formed on surfaces of teeth according to the present invention is phytic acid or a salt thereof, and acts as a gloss imparting agent. Phytic acid is also called as myo-inositol hexaphosphate and is a phosphoric acid compound. Among various phosphoric acid compounds, phytic acid or a salt thereof is especially excellent in the gloss imparting effect according to the present invention.

Examples of the salt include an alkali metal salt, such as sodium and potassium, and an ammonium salt or the like, and an alkali metal salt is preferred from viewpoints of taste and flavor.

An oral composition to be used in the present invention contains therein phytic acid or a salt thereof in an amount of 0.05% by weight to 18% by weight.

The content of phytic acid or a salt thereof in the composition is 0.05% by weight or more, and preferably 0.1% by weight or more, from a viewpoint of exerting fully the small solid product removing effect and the gloss imparting effect according to the present invention; and is 18% by weight or less, and preferably 10% by weight or less from a viewpoint of preventing decalcification of teeth and a viewpoint of taste and friction. In case where the composition for removing a solid product according to the present invention is a tooth paste, the content of phytic acid or a salt thereof in the tooth paste is preferably 0.05 to 5% by weight from a viewpoint of sense of use such as taste or friction. Note that the content of phytic acid or a salt thereof in the composition for removing a solid product according to the present invention is determined by neutralizing the acid using potassium hydroxide or sodium hydroxide, and converting the total used amount to an acid amount and thus-determined amount is used.

The content of a polyvalent cation in an oral composition used in the present invention is preferably suppressed to a low level, because a polyvalent cation makes phytic acid insoluble, and lowers the removing effect of the solid product, which should be avoided. The content of the polyvalent cation is measured by an ICP emission spectrometry (TOP emission spectrometer: Optima 5300DV, by Perkin Elmer Inc.), and the total content of polyvalent cations is preferably less than 0.1-fold mol relative to the phytic acid, and more preferably 0.02-fold mol or less. Namely, an agent supplying mainly a polyvalent cation, such as aluminium, calcium, magnesium, iron, and zinc, is preferably not used, and preferably a polyvalent cation is not contained substantially.

Further, since a cationic antibacterial agent, or an adsorbent, such as zeolite and active carbon, lowers the solid product removing effect of phytic acid, the content of thereof in an oral composition is preferably less than 0.001% by weight, more preferably 0.0001% by weight or less, and preferably not substantially contained.

The oral composition used in the present invention, as diluted with water to 30% by weight, has a pH of 5.5 to 6.5.

From a viewpoint of removing a solid product, suppressing decalcification of tooth surfaces, and exerting the gloss imparting effect when the composition is applied intraorally, the composition, as diluted with water to 30% by weight, has a pH of preferably 5.5 or more, and more preferably 5.8 or more; and from a viewpoint of exerting fully the gloss imparting effect by removal of the solid product, the pH is 6.5 or less and more preferably 6.2 or less.

Since the pH cannot be measured accurately for a high viscosity oral composition such as a tooth paste, a pH value for the composition as diluted with water to 30% by weight is employed as the pH of the composition. The dilution with water to 30% by weight is selected to simulate the situation of an intraoral application of the composition. Note that the water is purified water, and distilled water or ion exchanged water is used.

It is preferable to use a pH adjuster to adjust the pH of the composition in the aforementioned range. Examples of the pH adjuster include, insofar as it does not inhibit the removal of a solid product by phytic acid and can suppress decalcification of teeth, a salt of an organic acid such as acetic acid, fumaric acid, malic acid, lactic acid, gluconic acid and tartaric acid; salt of an inorganic acid such as phosphoric acid other than phytic acid (e.g. orthophosphoric acid), hydrochloric acid and sulfuric acid; a hydroxide such as sodium hydroxide; ammonia or ammonia water; lower alcanolamines; and a basic amino acid such as arginine and lysine, which may be used singly or in a combination of two or more. Among the listed pH adjusters, an organic acid and an inorganic acid (excluding phytic acid) should be contained preferably in an amount of 5% or less by weight with respect to phytic acid, and more preferably 1% or less, from a viewpoint of not inhibiting the solid product removing effect of phytic acid.

An oral composition used in the present invention preferably further contains erythritol. From a viewpoint of imparting gloss, the content of erythritol is preferably 10 to 60% by weight, more preferably 15 to 60% by weight, and even more preferably 20 to 60% by weight, and considering also fresh feel and taste, the content of 20 to 50% by weight is more preferable. From viewpoints of sense of use, fresh feel and taste, erythritol may be added to an oral composition according to the present invention in the form of powder or particle with the particle size of less than 35 μm.

As for the structure of erythritol, there are 3 isomers of L-erythritol, D-erythritol, and meso-erythritol, and any of them can be used in the present invention. Any normally available type of erythritol can be used, and examples thereof include a crystalline erythritol or the like yielded by fermentation of glucose followed by recrystallization. Examples of a commercially available crystalline erythritol include those from Nikken Chemical Co., Ltd., Mitsubishi-Kagaku Foods Corporation, Celestar Lexico-Sciences, Inc., and Cargill, Incorporated, or the like. A type with the large particle size is pulverized to adjust the particle size before using. Pulverization of erythritol is carried out generally using a roll mill, a hammer mill, a high-speed disintegrator, or a pulverizer, and in view of easier adjustment of the particle size and high productivity, disintegration by using a high-speed disintegrator or a hammer mill is preferred.

In case where an oral composition used in the present invention is a dentifrice, erythritol is preferably dispersed in the dentifrice in the form of powder or particle. Consequently, the erythritol is preferably supplied in the form of powder or particle at the final step of the production. From a viewpoint of a prolonged cooling feel in the oral cavity, the particle size is preferably not less than 45 μm and less than 355 μm, more preferably not less than 53 μm and less than 300 μm, and even more preferably not less than 75 μm and less than 250 Erythritol with the particle size of not less than 45 μm does not dissolve instantly in the mouth and a cooling feel lasts, which is preferable. Erythritol with the particle size of less than 355 μm can dissolve intraorally without difficulty and develop a cooling feel.

The particle size of erythritol is measured as follows.
Sieves: JIS standard sieves Φ75 mm
Openings: From top, sieves with the respective openings of 500 μm, 355 μm, 250 μm, 180 μm, 125 μm, 90 μm and 45 μm, as well as a sieve pan under the sieves
Shaker: Electromagnetic micro-vibro sifter M-2 (by Tsutsui Scientific Instruments Co., Ltd.)
Method: On the 500 μm sieve, 15 g of a sample is placed and sifted for 5 min using an electromagnetic shaker. The total amount of erythritol on the sieves with the respective openings of 250 μm, 180 μm, 125 μm, 90 μm and 45 μm is determined as the amount of erythritol with the particle size of not less than 45 μm and less than 355 μm.

A solid product formed on surfaces of teeth according to the present invention means a solid matter formed on surfaces of teeth with the thickness of less than 1 μm, which can be identified with electron microscope (SEM: S-4800, by Hitachi High-Technologies Corporation). The solid matter formed on surfaces of teeth with the thickness of less than 1 μm includes an aggregate of solid matters with the thickness of 500 nm or less. Such tiny solid product is a deposit of nano-scale solid products with the thickness of 200 nm or less, preferably 100 nm or less as obvious from an SEM photograph of FIG. 2(b), which are presumably formed by deposition of a component in saliva, such as a protein, calcium, and phosphorus. The formation of the tiny solid product by deposit is facilitated, by deterioration of intraoral environment due to aging, or decrease of secretion of saliva, and the like.

As described above, a solid product on tooth surfaces with the height of less than 1 μm, as well as a solid product with the height of 0.5 μm or less can be removed by the method according to the present invention without creating roughness on tooth surfaces, and as the result good gloss can be imparted to teeth. Thus, a composition according to the present invention can selectively remove a nano-scale solid product without damaging tooth surfaces, and consequently exert a remarkable effect to make tooth surfaces smooth and impart gloss to teeth.

As described above, the present inventors have found that an oral composition containing (A) phytic acid or a salt thereof in an amount of 0.01 to 10% by weight, and (B) erythritol in an amount of 3 to 60% by weight, wherein B/A=5 to 1000, can have an excellent whitening effect on teeth and a gloss imparting effect on teeth, without a frictional feel of teeth but with a good sense of use.

An oral composition according to the present invention contains therein 0.01 to 10% by weight of (A) phytic acid or a salt thereof. From a standpoint of tooth whitening effect and gloss imparting effect, the content of (A) phytic acid or a salt thereof is preferably 0.05% by weight or more, and more preferably 0.1% by weight or more; and from standpoints of taste and coloration, the content of (A) phytic acid or a salt thereof in the composition is preferably 5% by weight or less, and more preferably 2% by weight or less. In case where an oral composition according to the present invention is a mouthwash, the content of (A) phytic acid or a salt thereof is preferably 3% by weight or less, and more preferably 1% by weight or less. The content of phytic acid or a salt thereof according to the present invention is determined by neutralizing the acid using potassium hydroxide or sodium hydroxide and converting the total used amount to an acid amount and thus-determined amount is used.

An oral composition according to the present invention contains (B) erythritol in an amount of 3 to 60% by weight. By containing erythritol in this range, a frictional feel of teeth caused by phytic acid can be improved and a good sense of use can be obtained. The content of erythritol is more preferably 4 to 50% by weight, and even more preferably 5 to 45% by weight. In case where an oral composition according to the present invention is a mouthwash, the content of erythritol is preferably 30% by weight or less, and more preferably 20% by weight or less.

The weight ratio (B/A) of the component (B) to the component (A) according to the present invention is important in terms of the improving effect of frictional feel due to phytic acid and the sense of use, and is preferably 5 to 1000, more preferably 10 to 800, even more preferably 15 to 500, and even more preferably 20 to 500. In case where an oral composition according to the present invention is a mouthwash, the weight ratio (B/A) of the component (B) to the component (A) is preferably 5 to 300, more preferably 10 to 300, even more preferably 15 to 300, and even more preferably 20 to 300.

As described hereinabove, phytic acid is one of phosphoric acid compounds, and although another phosphoric acid compound, such as polyphosphoric acid, causes also a frictional feel of teeth, the frictional feel by phytic acid is unique, and mixing of erythritol with polyphosphoric acid cannot improve the frictional feel of teeth caused by polyphosphoric acid. Consequently, it is so considered that the effect according to the present invention is unique to the combination of phytic acid and erythritol.

Further, into an oral composition to be used in the present invention, a fluoride (a fluorine ion-supplying compound), such as sodium fluoride, potassium fluoride, ammonium fluoride, and sodium monofluorophosphate may be added to the extent (content, formulation, etc.) that the gloss imparting effect of phytic acid or a salt thereof is not inhibited. It is preferable that a fluoride is not contained in the composition, or the content is less than 500 ppm, and more preferably. 300 ppm or less in terms of fluorine atom.

In an oral composition to be used in the present invention, in addition to the aforementioned components, for example, a foaming agent, a foaming assistant, a abrasive, a wetting agent, a thickening agent, a gelling agent, a binding agent, an extending agent, a sweetening agent, a preservation agent, an antibacterial agent, medicinally active ingredient, a pigment, a colorant, a flavor and the like may be contained, appropriately to produce the composition in various formulations. Further, the combined use with a conventional whitening ingredient, such as polyethylene glycol, is not restricted.

An oral composition to be used in the present invention may be formulated to, for example, a solution, a gel, or a paste, and used as an oral composition, such as a powder dentifrice, a wet-powder dentifrice, a tooth paste, a liquid dentifrice, and a mouthwash; as a food, such as chewing gum, troche, and candy; or as an oral sanitary device such as a dental floss by impregnating into a sheet, a cloth, a fiber, etc.

Any of the formulations may contain polyethylene glycol, propylene glycol, glycerin, sorbitol, maltitol, xylitol, lactitol, etc. for purposes of a wetting agent, or a thickening agent, etc.

One or more of sodium carboxymethyl cellulose, hydroxyethyl cellulose, carboxy vinyl polymer, xanthan gum, carrageenan, sodium alginate, hydroxypropylcellulose, guar gum, sodium chondroitin sulfate, etc, may be contained as a thickening agent for a solution composition, a gelling agent for a gel composition, and a binding agent for a paste composition. Among them a binding agent other than sodium alginate is preferably selected from a viewpoint, of exerting fully the gloss imparting effect of phytic acid or a salt thereof.

Further, in case where the salt concentration is high due to a buffer solution system, one or more of nonionic polymers, such as hydroxyethylcellulose, guar gum, and hydroxypropylcellulose may be contained.

In case where the composition according to the present invention is a tooth paste, the content of phytic acid or a salt thereof is preferably 0.05 to 5% by weight from a viewpoint of the sense of use. The viscosity at 25° C. of the tooth paste is preferably 10 to 300 Pa·s, more preferably 20 to 250 Pa·s, and even more preferably 3.0 to 200 Pa·s from a viewpoint of adequate gloss imparting effect. In the above range, even if the content of phytic acid is 5% by weight or less, since the intraoral dispersibility is increased, the phytic acid can spread rapidly and act effectively on a tiny solid product built up on tooth surfaces. In case where the viscosity is too low, the paste flows down from a toothbrush, impairing the usability, and in case where the viscosity is too high, the intraoral dispersibility becomes poor, and the full solid product removing effect or gloss imparting effect cannot be realized. The viscosity is measured by a Helipath viscometer at a measuring temperature of 25° C. under the measuring conditions rotor C; 2.5 r/min; for 1 min.

In case where the composition according to the present invention is dentifrices, granules can be added. But, from a viewpoint of not inhibiting the gloss development through suppression of forming tiny roughness on tooth enamel surfaces, preferably the granule is not added, or the granule is contained, whose disintegration strength in a dry state is 10 g/granule or less, and more preferably that in the coexistence of water is 10 g/granule or less. Further, to the extent that the gloss development effect according to the present invention is not inhibited, a abrasive can be contained, and the use of a silica abrasive, such as hydrous silica, anhydrous silica, and silica gel, is preferable.

For application of the composition according to the present invention to teeth, two cases are possible, namely the composition may be applied as it is, or it may be applied in a diluted state to about 30% by weight with water or saliva, etc. More specifically, in case of a mouthwash, it may be applied to teeth without dilution, while in case of a tooth paste or the like, it is applied to teeth in a diluted state to about 30% by weight with saliva.

When such a composition is applied to human teeth for 10 sec to 10 hours (in case of a mouthwash for 10 sec or longer, in case where the composition is a dentifrice for 30 sec or longer, and in case of an applicator for 5 min or longer), for example, one to five times per day, and preferably for a period of 1 week to 16 weeks, the surfaces of tooth enamel can be smoothened without damaging the tooth enamel itself by removing selectively a nano-scale (less than 1 μm) solid product on surfaces of tooth enamel, and natural gloss of teeth themselves can appear by increasing reflected light from the surfaces of tooth enamel. Namely, despite the long-lasting use or the repeated uses, teeth with natural luster or gloss can be obtained, while suppressing damages on the surfaces of tooth enamel.

As hereinabove described, the effects of the composition according to the present invention to whiten teeth and to impart natural luster or gloss to teeth are believed to be caused by removal of a nano-scale solid product on the surfaces of tooth enamel. Furthermore, it is believed that the composition according to the present invention has an activity to reconstruct an interprismatic space in the tooth enamel, and by such a reconstructive activity of the interprismatic space a tooth whitening effect can be also obtained.

The enamel of a tooth is constituted of an aggregate of rods called enamel prisms constituted of polycrystalline hydroxyapatite. Generally in the juvenile period, there is a space (vacancy) in enamel between enamel prisms, namely an interprismatic space, which is filled with water, saliva components or the like. In such a tooth, incident light to the enamel is scattered due to a large difference in refractive index between an enamel prism and vacancy in interprismatic space, and the tooth appears white.

However, in case where a dissolved substance in saliva continues to deposit in an interprismatic space in a surface layer of tooth enamel due to aging or otherwise, the interprismatic space is filled up and as the result the refractive index difference between the enamel prism and the interprismatic space decreases, so that the transparency of the enamel increases and the incident light reaches easily the dentin, which is yellow to brown and located deep under the enamel, to thereby make the tooth appear yellowish.

Consequently, the present inventors have speculated that by removing selectively a substance existing in the interprismatic space in a surface layer of the tooth enamel (hereinafter referred to as "interprismatic substance") from the interprismatic space, the interprismatic space vacancies can be reconstructed, while suppressing damages on enamel prisms themselves constituting the enamel, and the reflected light from the inside of the enamel is increased by light scattering at interprismatic space vacancies to thereby obtain naturally white teeth.

Consequently, the composition according to the present invention was applied to teeth and its action on the interprismatic space was evaluated to find that the composition according to the present invention has an excellent effect in promoting reconstruction of the interprismatic space as shown in Examples below.

EXAMPLES

In the following examples, % means % by weight.

Test Example 1

Tooth Surface Conditions after Treatment with Composition

Table 1 shows the respective components and the contents thereof in a tooth paste containing 16 of phytic acid. A tooth paste (Example 1) with the components mixed was prepared as a test solution. Polyvalent cations, such as magnesium, aluminium, and calcium, in the test solution of Example 1 were measured by an IPC emission spectrometry to find that the amount was less than 0.1-fold mol relative to the phytic acid. As Comparative Example 1, a dentifrice without phytic acid was prepared as a test solution.

The pH of the test solution of Example 1 is the pH after dilution to 30% by weight with ion exchanged water. Since Comparative Example 1 does not contain phytic acid, the pH was neutral and pH adjustment by using potassium hydroxide was not conducted. A tooth used for testing was a human (extracted) tooth, which was not subjected to a cleaning treatment, such as abrasion.

A brushing treatment was conducted, according to the following procedure. Immersing a human tooth (extracted tooth) in each test solution at room temperature for 2 min and brushing was carried out with a toothbrush (Clear Clean multi-care toothbrush, hardness normal, by Kao Corporation). After that the tooth was immersed in artificial saliva at room temperature for 8 hours. The above cycle was repeated 28 times. As the artificial saliva, an aqueous solution of calcium chloride (1.0 mM), potassium hydrogenphosphate (0.9 mM), and HEPES (4-(2-hydroxyethyl)-1-piperazineethanesulfonic acid) (2.0 mM), adjusted to pH=7 with potassium hydroxide, was used. The change ($\Delta$ brightness) of brightness value between before and after the above 26 cycles was measured. The change ($\Delta$ brightness) was determined by (brightness after the immersion–brightness before the immersion). In the above, 3 human teeth (extracted teeth) were used, and $\Delta$ brightness was evaluated by the average value of the measurements of the 3 human teeth.

The brightness was measured by a method, in which the surface reflection intensity was measured by image analysis using polarized light. As a device for picking up an evaluation image, an assembly of a digital single-lens reflex camera (Nikon D70); a lens of Ai AF Micro-Nikkor 105 mm F2.8D; and a stroboscopic light source of Wireless Remote Speedlight SB-R200 (all by Nikon Corporation) was used. Plastic polarizing plates (by Edmund Optics Inc.) were placed in front of the light source of Speedlight and the lens crossing the transmission axes at an angle of 30° for imaging. The average brightness of a highlight part of the picked-up image was determined using Adobe Photoshop CS3 (by Adobe Systems Incorporated). The larger value of the brightness means the higher gloss.

Figure 2:
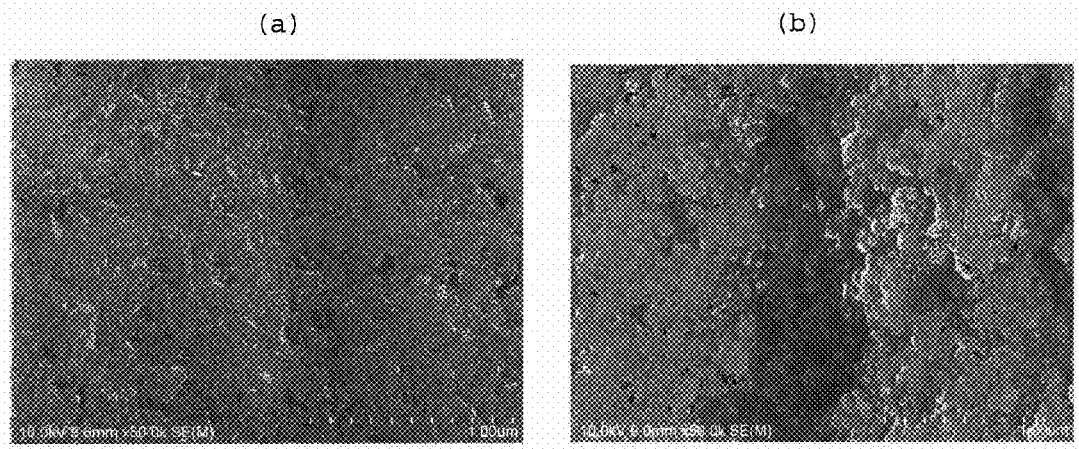
FIG. 2 is photographs of a tooth surface after a brushing treatment, observed with electron microscope (×50,000).

The roughness concerning the surface conditions in Table 1 was evaluated megascopically with a magnifying glass (magnification ×10) on a tooth after the 28-cycle brushing treatments. Meanwhile, FIG. 1 and FIG. 2 show photographs of the tooth surface before and after the brushing treatments observed with electron microscope (SEM: S-4800, by Hitachi High-Technologies Corporation), wherein tooth surface photographs of (a) after the brushing treatment with the test solution according to Example 1; (b) after the brushing treatment with the test solution according to Comparative Example 1; (c) after the brushing treatment with immersion in ion exchanged water without using the test solution; and (d) before the brushing treatment; are shown. FIG. 1 is photographs of the magnification ×50, and FIG. 2 is photographs of the magnification ×50,000.

As shown in FIG. 1, in the photograph (c) after the treatment by brushing without using a test solution, a solid product smaller than 1 mm (μm-scale) can be recognized on the tooth surface. In the photograph (b) after the brushing treatment with the test solution according to Comparative Example 1, a residual solid product is recognized partly as darkening. In the photograph (a) after the brushing treatment with the test solution according to Example 1, the surface is smooth, and a solid product is not recognizable. On the other hand, concerning the photographs in FIG. 2, in the photograph (b) after the brushing treatment with the test solution according to Comparative Example 1, a solid product smaller than 1 μm is recognizable, but in the photograph (a) after the brushing treatment with the test solution according to Example 1, a solid product smaller than 1 μm is hardly recognizable. Further, the brightness of a human tooth does not change significantly after the brushing treatment with the test solution according to Comparative Example 1, while the $\Delta$ brightness of a human tooth after the brushing treatment according to Example 1 was high and the gloss imparting effect was recognized. Further, a human tooth after the brushing treatment according to Example 1 appeared whiter than a human tooth after the brushing treatment according to Comparative Example 1. Consequently, it can be presumed that by removing a solid product of less than 1 μm formed on tooth surfaces, not only the tooth becomes white, but also total reflected light can be increased and high brightness, namely high gloss or luster can be obtained.

TABLE 1

| Components (% by weight) | Ex. 1 | Com. Ex. 1 |
|---|---|---|
| Phytic acid | 1 | 0 |
| Sorbitol solution (70%) | 30 | 30 |
| Polyethylene glycol (PEG600) | 5 | 5 |
| Sodium saccharin | 0.1 | 0.1 |
| Sodium carboxymethylcellulose | 1.5 | 1.5 |
| Thickening silica | 5 | 5 |
| Abrasive silica | 15 | 15 |
| Sodium lauryl sulfate | 1.5 | 1.5 |
| Flavor | 1 | 1 |

TABLE 1-continued

| Components (% by weight) | Ex. 1 | Com. Ex. 1 |
|---|---|---|
| Potassium hydroxide solution (48%) | q.s. | 0 |
| Purified water | q.s. | q.s. |
| Total | 100 | 100 |
| pH | 6.0 | — |
| Δ brightness (*1) | 5.8 | 0.5 |
| Test with extracted tooth (Surface conditions observed with magnifying glass) (*1) | Smooth | Solid product existing before the test remains |

*1: Brightness and surface conditions after brushing treatment

Test Example 2

Relationship with Content of Another Organic Acid

Table 2 shows the respective components and the contents thereof in a tooth paste containing 1% of phytic acid. A tooth paste with the components mixed was prepared as a test solution. Polyvalent cations, such as magnesium, and aluminium, in the test solution were measured by an IPC emission spectrometry to find that the amount was less than 0.1-fold mol relative to the phytic acid.

(1) The respective tooth pastes were diluted to 30% by weight with ion exchanged water and used as test solutions. Human teeth were immersed into the test solutions without brushing at room temperature for 48 hours, and the brightness before and after the immersion was measured. The change (Δ brightness) of the brightness between before and after the immersion was determined by (brightness after the immersion−brightness before the immersion). As a human tooth, an extracted tooth, which was not subjected to a cleaning treatment, such as abrasion, was used as in Test Example 1. The measurement of the change (Δ brightness) of the brightness between before and after the immersion in the test solution, and the observation of the tooth surface roughness were conducted as in Test Example 1.

TABLE 2

| Components (% by weight) | Ex. 1 | Ex. 2 | Ex. 3 | Ex. 4 | Ex. 5 | Ex. 6 | Ex. 7 | Ex. 8 | Ex. 9 | Ex. 10 |
|---|---|---|---|---|---|---|---|---|---|---|
| Phytic acid | 1 | 1 | 1 | 0.05 | 0.1 | 10 | 18 | 1 | 1 | 1 |
| Lactic acid | 0 | 0 | 0 | 0 | 0 | 0 | 0 | 0 | 0 | 0 |
| Sorbitol solution (70%) | 30 | 30 | 30 | 30 | 30 | 30 | 30 | 30 | 30 | 30 |
| Erythritol | 0 | 0 | 0 | 0 | 0 | 0 | 0 | 20 | 10 | 5 |
| Polyethylene glycol (PEG600) | 5 | 5 | 5 | 5 | 5 | 5 | 5 | 5 | 5 | 5 |
| Sodium saccharin | 0.1 | 0.1 | 0.1 | 0.1 | 0.1 | 0.1 | 0.1 | 0.1 | 0.1 | 0.1 |
| Sodium carboxymethylcellulose | 1.5 | 1.5 | 1.5 | 1.5 | 1.5 | 1.5 | 1.5 | 1.5 | 1.5 | 1.5 |
| Thickening silica | 5 | 5 | 5 | 5 | 5 | 5 | 5 | 5 | 5 | 5 |
| Abrasive silica | 15 | 15 | 15 | 15 | 15 | 15 | 15 | 15 | 15 | 15 |
| Sodium lauryl sulfate | 1.5 | 1.5 | 1.5 | 1.5 | 1.5 | 1.5 | 1.5 | 1.5 | 1.5 | 1.5 |
| Flavor | 1 | 1 | 1 | 1 | 1 | 1 | 1 | 1 | 1 | 1 |
| Potassium hydroxide solution (48%) | q.s. | q.s. | q.s. | q.s. | q.s. | q.s. | q.s. | q.s. | q.s. | q.s. |
| Purified water | q.s. | q.s. | q.s. | q.s. | q.s. | q.s. | q.s. | q.s. | q.s. | q.s. |
| Total | 100 | 100 | 100 | 100 | 100 | 100 | 100 | 100 | 100 | 100 |
| pH | 6.0 | 6.5 | 5.5 | 6.0 | 6.0 | 6.0 | 6.0 | 6.0 | 6.0 | 6.0 |
| Δ brightness (*2) | 6.2 | 6.1 | 6.0 | 4.5 | 5.8 | 6.1 | 6.0 | 7.6 | 6.7 | 6.5 |
| Test with extracted tooth (Surface conditions observed with magnifying glass) | Smooth | Smooth | Smooth | Smooth | Smooth | Smooth | Smooth | Smooth | Smooth | Smooth |
| Test with extracted tooth (Interprismatic space conditions observed with SEM) | Vacant in interprismatic space | Vacant in interprismatic space | Vacant in interprismatic space | Vacant in interprismatic space | Vacant in interprismatic space | Vacant in interprismatic space | Vacant in interprismatic space | Vacant in interprismatic space | Vacant in interprismatic space | Vacant in interprismatic space |

(*2) Change of brightness between before and after immersion in test solution

TABLE 3

| | Phytic acid (Example 1) | Orthophosphoric acid | Polyphosphoric acid | Phytic acid 70% Polyphosphoric acid 30% | Phytic acid 90% Polyphosphoric acid 10% |
|---|---|---|---|---|---|
| Δ brightness (*2) | 6.0 | 0.5 | <0 | <0 | <0 |
| Test with extracted tooth (Surface conditions observed with magnifying glass) | Smooth | No change before and after treatment | Deep roughness on treated surface | Deep roughness on treated surface | Roughness on treated surface |

*2: Change of brightness between before and after immersion in test solution

With respect to the test solution of the tooth paste according to Example 1 in Table 2 and test solutions prepared by using the same components and composition as Example 1, except that the 1% by weight of phytic acid in Example 1 was replaced with 1% by weight of orthophosphoric acid, 1% by weight of polyphosphoric acid, and 1% by weight of a mixture of phytic acid and polyphosphoric acid respectively, human teeth were immersed at room temperature for 48 hours in the respective test solutions as in Test Examples 2, and the change (Δ brightness) of the brightness measured before and after the immersion, the surface conditions of the extracted teeth after the immersion are shown in Table 3. As obvious from Table 3, with respect to a human tooth treated with a test solution containing polyphosphoric acid and a mixture of phytic acid and polyphosphoric acid, roughness of the enamel surface indicating damages was recognized and Δ brightness was minus, namely the gloss decreased. With respect to a human tooth treated with a test solution containing orthophosphoric acid, significant damages of the enamel surface was not observed, but a solid product remained on tooth surfaces and the Δ brightness value was small, indicating no gloss imparting effect. While, in case of phytic acid the Δ brightness value was large, the tooth surface was also smooth, showing no sign of damages, and a high gloss imparting effect was recognized. Additionally, pyrophosphoric acid and metaphosphoric acid were tested in the same manner as polyphosphoric acid, but the tooth surface was damaged and no gloss imparting effect was recognized.

Consequently, phytic acid is most excellent among these phosphoric acid compounds in terms of gloss imparting effect, which is considered a high selective removing effect of a solid product on tooth surfaces due to the increased total reflected light. Further, the following tests were carried out for test solutions containing phytic acid.

Test Example 3 pH of Composition and Content of Phytic Acid in Composition (1) Composition and Preparation of Test Sample The respective components and the contents thereof in the tooth pastes of Examples 1 to 10 are shown in Table 2, and those of Comparative Examples 2 to 9 are shown in Table 4. The pH of the tooth paste (test solution) is the pH after dilution to 30% by weight with ion exchanged water.

The content of phytic acid in a tooth paste was set at 1% by weight, and test solutions of tooth pastes (Example 1 to 3 and Comparative Examples 2 to 6), whose pHs after dilution to 30% by weight with ion exchanged water were adjusted to 3.0, 4.0, 5.0, 5.5, 6.0, 6.5, 7.0, and 8-0 respectively, were prepared. The content of polyvalent cations, such as magnesium and aluminium, in the respective test solutions were measured by an IPC emission spectrometry to find that the amount was less than 0.1-fold mol relative to phytic acid.

Further, the respective test solutions of tooth pastes (Example 4 to 7 and Comparative Examples 7 to 9) with the contents of phytic acid of 0, 0.05, 0.1, 10, 18, 19, and 20% by weight and the pH adjusted to 6.0 were prepared. A control containing 1% by weight of phytic acid was Example 2. The content of polyvalent cations, such as magnesium and aluminium, in the respective test solutions were measured by an IPC emission spectrometry to find that the amount was less than 0.1-fold mol relative to the phytic acid.

The conditions of human teeth to be used for tests were similar to Test Example 1, and measurement of the change (Δ brightness) of the brightness between before and after the immersion in each test solution, and measurement of the tooth surface conditions (surface roughness) were conducted as in Test Example 1.

As shown by Comparative Examples 2 to 4, in case where the pH is in a range less than 5.5, roughness is generated on tooth surfaces, and the brightness of tooth surfaces decreases. Meanwhile, the teeth treated by a test solution with the pH of 7.0 or more as in Comparative Example 5 or 6, the roughness is not generated on surfaces, but no solid product removing effect was recognized, the Δ brightness was low and good gloss did not appear. In contrast thereto, in case of the composition for removing a solid product according to the present invention, the pH was in a range of 5.5 or more and 6.5 or less, and under such conditions, not only a tooth looked white, but also the Δ brightness became sufficiently large, indicating a high gloss imparting effect, and a smooth surface was also observed by an SEM observation.

As described, above, phytic acid (inositol hexaphosphate) or a salt thereof showing a pH range of 5.5 to 6.5 according to the present invention, gives almost no damage to enamel surfaces, and can remove selectively a solid product of less than 1 μm formed on surfaces.

With respect to the concentration of phytic acid, even at 0.05% the tooth could be whitened, and further the Δ brightness was as high as 4.5, indicating a high gloss imparting effect; and at 0.1% or more the A brightness became 5.8 or more, indicating a high gloss imparting effect. However, as shown in Comparative Examples 8 and 9, at a concentration of 19% by weight or more, roughened tooth surfaces were observed. Further, also from a viewpoint of taste, the concentration of 10% by weight or less is preferable, and 5% by weight or less is more preferable. In Comparative Example 7, in which 1% of lactic acid instead of phytic acid was used the tooth surfaces were roughened and the gloss decreased (the Δ brightness was minus).

Further, in Example 8 to Example 10, in which erythritol was contained, the Δ brightness was higher than in Example 1 containing the same amount of phytic acid at the same pH, the Δ brightness values of Examples 8 to 10 were highest among Examples 1 to 10. Improvement of the gloss imparting effect was thus recognized by the use of erythritol contained in addition to phytic acid.

TABLE 4

| Components (% by weight) | Com. Ex. 2 | Com. Ex. 3 | Com. Ex. 4 | Com. Ex. 5 | Com. Ex. 6 | Com. Ex. 7 | Com. Ex. 8 | Com. Ex. 9 |
|---|---|---|---|---|---|---|---|---|
| Phytic acid | 1 | 1 | 1 | 1 | 1 | 0 | 20 | 19 |
| Lactic acid | 0 | 0 | 0 | 0 | 0 | 1 | 0 | 0 |
| Sorbitol solution (70%) | 30 | 30 | 30 | 30 | 30 | 30 | 30 | 30 |
| Polyethylene glycol (PEG600) | 5 | 5 | 5 | 5 | 5 | 5 | 5 | 5 |
| Sodium saccharin | 0.1 | 0.1 | 0.1 | 0.1 | 0.1 | 0.1 | 0.1 | 0.1 |

TABLE 4-continued

| Components (% by weight) | Com. Ex. 2 | Com. Ex. 3 | Com. Ex. 4 | Com. Ex. 5 | Com. Ex. 6 | Com. Ex. 7 | Com. Ex. 8 | Com. Ex. 9 |
|---|---|---|---|---|---|---|---|---|
| Sodium carboxymethylcellulose | 1.5 | 1.5 | 1.5 | 1.5 | 1.5 | 1.5 | 1.5 | 1.5 |
| Thickening silica | 5 | 5 | 5 | 5 | 5 | 5 | 5 | 5 |
| Abrasive silica | 15 | 15 | 15 | 15 | 1.5 | 15 | 15 | 15 |
| Sodium lauryl sulfate | 1.5 | 1.5 | 1.5 | 1.5 | 1.5 | 1.5 | 1.5 | 1.5 |
| Flavor | 1 | 1 | 1 | 1 | 1 | 1 | 1 | 1 |
| Potassium hydroxide solution (48%) | q.s. | q.s. | q.s. | q.s. | q.s. | q.s. | q.s. | q.s. |
| Purified water | q.s. | q.s. | q.s. | q.s. | q.s. | q.s. | q.s. | q.s. |
| Total | 100 | 100 | 100 | 100 | 100 | 100 | 100 | 100 |
| pH | 3.0 | 4.0 | 5.0 | 7.0 | 8.0 | 6.0 | 6.0 | 6.0 |
| Δ brightness(*2) | <0 | <0 | 2.8 | 2.0 | 1.5 | <0 | * | * |
| Test with extracted tooth (Surface conditions observed with magnifying glass) | Roughened | Roughened | Roughened | Solid product remains*1 | Solid product remains*1 | Roughened | Roughened | Roughened |
| Test with extracted tooth (Interprismatic space conditions observed with SEM) | Larger than natural vacancy in interprismatic space | Larger than natural vacancy in interprismatic space | Slightly larger than natural vacancy in interprismatic space | No change | No change | Larger than natural vacancy in interprismatic space | Slightly larger than natural vacancy in interprismatic space | Slightly larger than natural vacancy in inteiprismatic space |

*: Due to uneven roughness conditions on surfaces, the brightness is regionally 5 or <0.
*1 Solid product existing before the test remains.
(*2) Change of brightness between before and after immersion in test solution Test Example 4

Content of Polyvalent Cations in Composition

As the test solutions, the tooth pastes of Example 1, and Comparative Examples 10 and 11 shown in Table 5 were prepared. The test solution of Example 1 was prepared from the tooth paste containing 1% by weight of phytic acid but substantially no polyvalent cation, and the test solution of Comparative Example 9 was prepared by adding thereto magnesium and aluminium in the total amounts of 5,000 ppm, and that of Comparative Example II by adding thereto magnesium and aluminium in the total amounts of 500 ppm. The pH values of the tooth pastes. (test solutions) were those after dilution to 30% by weight with ion exchanged water. The contents of polyvalent cations in Example 1 were magnesium 18.4 ppm (1.05-fold mol relative to phytic acid) and aluminium 16.4 ppm (0.04-fold mol relative to phytic acid), and the total amount of polyvalent cations was 36.8 ppm, which was less than 0.1-fold mol relative to phytic acid; 5,000 ppm of magnesium was added for Comparative Example 9, and the content of polyvalent cations was 13.6-fold mol or more relative to phytic acid; and 500 ppm of aluminium was added for Comparative Example 10, and the content of polyvalent cations was 1.2-fold mol or more relative to phytic acid.

The conditions of human teeth to be used for tests were similar to Test Example 1, and measurement of the change (Δ brightness) of the brightness between before and after the immersion in each test solution, and measurement of the tooth surface roughness conditions were conducted as in Test Example 1.

In Comparative Example 10 containing 5,000 ppm of magnesium, and Comparative Example 11 containing 500 ppm of aluminium, a condition that a solid product existing before the test remained on the tooth surface was recognized, and the teeth looked yellowish and the Δ brightness was low in comparison with Example 2, indicating that the solid product removing effect and the gloss imparting effect by phytic acid were suppressed.

As described above, phytic acid or a salt thereof in the absence of a polyvalent cation or in the presence of a polyvalent cation in an amount of less than 0.1-fold mol relative to phytic acid can, without deteriorating the solid product removing effect of phytic acid, offer the effect of tooth whitening, and function sufficiently as a gloss imparting agent.

TABLE 5

| Components (% by weight) | Ex. 1 | Com. Ex. 10 | Com. Ex. 11 |
|---|---|---|---|
| Phytic acid | 1 | 1 | 1 |
| Lactic acid | 0 | 0 | 0 |
| Sorbitol solution (70%) | 30 | 30 | 30 |
| Polyethylene glycol (PEG600) | 5 | 5 | 5 |
| Sodium saccharin | 0.1 | 0.1 | 0.1 |
| Sodium carboxy-methyl-cellulose | 1.5 | 1.5 | 1.5 |
| Thickening silica | 5 | 5 | 5 |
| Abrasive silica | 15 | 15 | 15 |
| Sodium lauryl sulfate | 1.5 | 1.5 | 1.5 |
| Flavor | 1 | 1 | 1 |
| Potassium hydroxide solution (48%) | q.s. | q.s. | q.s. |
| Mg (ppm) | 34.8 | 5000 | 500 |
| Al (ppm) | | 5000 or more | 500 or more |
| Purified water | q.s. | q.s. | q.s. |
| Total | 100 | 100 | 100 |
| pH | 6.0 | 6.0 | 6.0 |
| Δ brightness (*2) | 6.2 | 2.1 | 4.1 |
| Surface conditions observed with magnifying glass | Smooth | Solid product existing before the test remains | Solid product existing before the test remains slightly |

*2: Change of brightness between before and after immersion in test solution

Test Example 5

Viscosity of Dentifrice

The tooth pastes of Examples 11 to 13 shown in Table 6 were prepared as test solutions. The content of magnesium and aluminium in the respective test solutions was measured by IPC emission spectrometry to find that the content was less than 0.1-fold mol relative to phytic acid. Based on Example 11, in which the content of phytic acid in the tooth paste was set at 1% to by weight and the viscosity was adjusted to 90 Pa·s, the quantity and quality (degree of etherification) of sodium carboxymethylcellulose, and purified water were adjusted to prepare the tooth paste of Example 12 so as to have 220 Pa·s, and the tooth paste of Example 13 so as to have 400 Pa·s. The viscosity was measured using a Helinath viscometer under the measuring conditions: a measuring temperature of 25° C., with a rotor C, at 2.5 r/min (2.5 rpm), and for 1 min. The test procedure was as follows each test solution was diluted to 30% by weight with ion exchanged water, a human tooth was immersed in the diluted test solution for 48 hours, and the brightness before and after the immersion was measured to determine the change (Δ brightness) of the brightness between before and after the immersion (brightness after immersion−brightness before immersion). The conditions of human teeth were similar to Test Example 1, and measurement of the change (Δ brightness) of the brightness between before and at ter the immersion in each test solution, and observation of the roughness of tooth surfaces were conducted as in Test Example 1. The dilution of the test solutions with ion exchanged water to 3.0% by weight is to simulate a situation of intraoral application of a tooth paste, and in case where the tooth pastes with the compositions of Examples 11 to 1.3 are diluted to 30% by weight, the viscosities becomes ⅛ to 1/10. For example, the viscosity of the tooth paste of Example 10 diluted to 30% by weight is about 30 Pa·s. In any of Examples 11 to 13, it was recognized that the surface was smooth and the tooth was whitened, and that the Δ brightness of Example with lower viscosity was higher and especially high Δ brightness was obtained from a tooth paste with the viscosity of 250 Pa·s or less,

TABLE 6

| Components (% by weight) | Ex. 11 | Ex. 12 | Ex. 13 |
|---|---|---|---|
| Phytic acid | 1 | 1 | 1 |
| Sorbitol solution (70% aq. solution) | 35 | 35 | 35 |
| Polyethylene glycol (PEG600) | 5 | 5 | 5 |
| Sodium saccharin | 0.1 | 0.1 | 0.1 |
| Sodium carboxy-methylcellulose | 1.5 | 1.5 | 1.5 |
| Xanthan gum | 0.1 | 0.1 | 0.1 |
| Abrasive silica | 25 | 25 | 25 |
| Sodium lauryl sulfate | 1.5 | 1.5 | 1.5 |
| Flavor | 1 | 1 | 1 |
| Potassium hydroxide solution (48%) | 0 | 2.5 | 1 |
| Sodium hydroxide solution (48%) | 0.4 | 0 | 0 |
| Purified water | 30.1 | To be adjusted | To be adjusted |
| Total | 100 | 100 | 100 |
| Viscosity (Pa · s) | 90 | 220 | 400 |
| pH | 6.0 | 6.3 | 5.8 |
| Δ brightness (*3) | 8.5 | 6.9 | 4.8 |
| Surface conditions observed with magnifying glass | Smooth | Smooth | Smooth |

*3: Change of brightness between before and after immersion in test solution diluted to 30% by weight with ion exchanged water Test Example 6

Observation of Tooth Interprismatic Space by SEM

Figure 3:
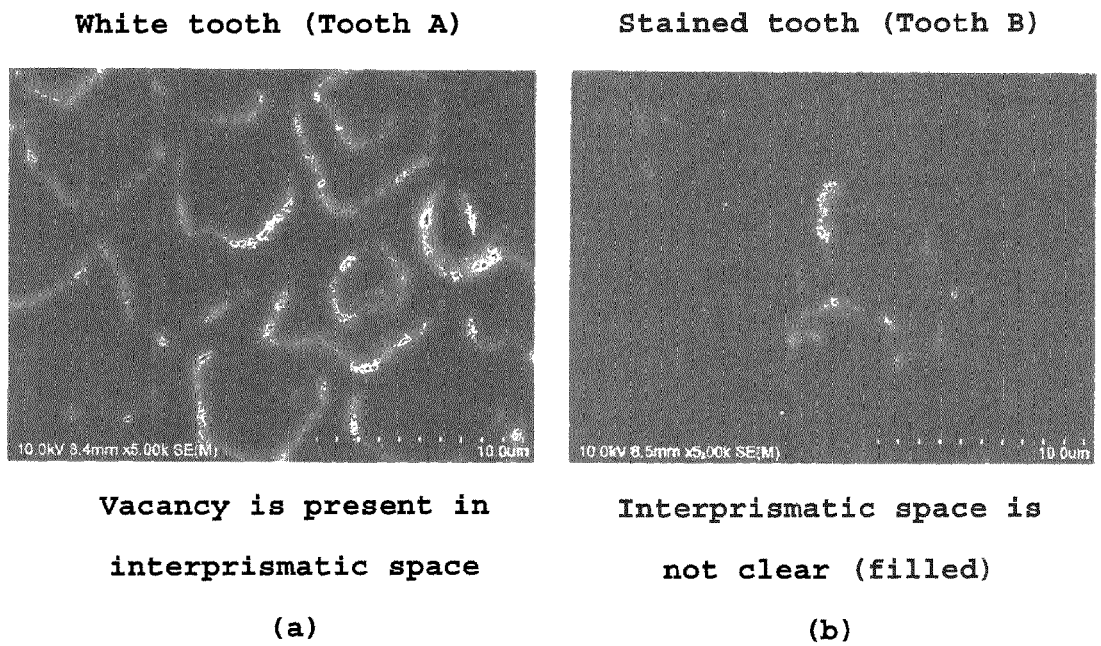
FIG. 3 is photographs, observed with SEM, (a) a white tooth A, and (b) a stained tooth B.
Figure 4:
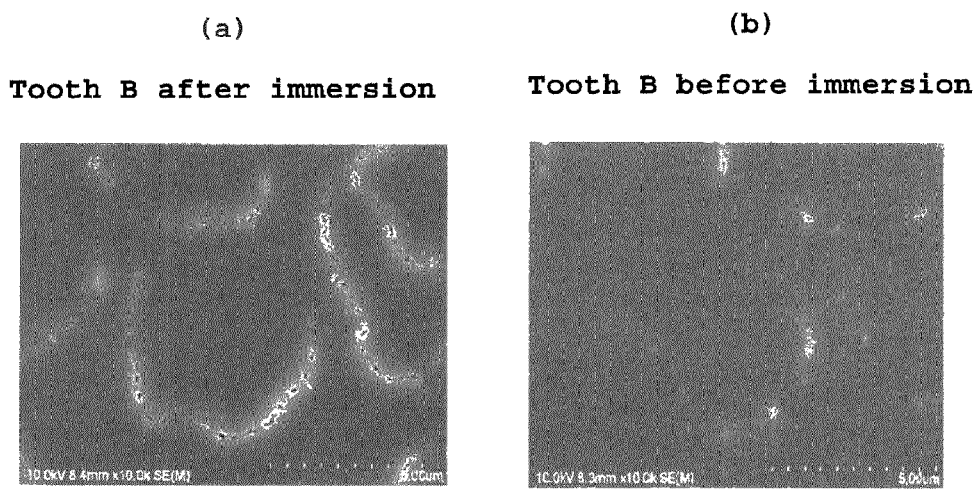
FIG. 4 is photographs, observed with SEM, of (a) the tooth B after immersion in a composition containing phytic acid, and (b) the tooth B before the immersion.

Photographs observing tooth interprismatic spaces with electron microscope (SEM: S-4800, by Hitachi High-Technologies Corporation) are shown in FIG. 3 and FIG. 4. FIG. 3(a) shows a photograph of a white tooth A (a teenage human tooth) and FIG. 3(b) shows a photograph of a stained tooth B (a tooth of human in 50 s) observed with electron microscope (SEM).

As obvious from photographs FIGS. 3(a) and 3(b), on the white tooth A interprismatic spaces can be observed, but on the stained tooth B the interprismatic spaces can be hardly observed any more.

FIG. 4(b) shows a photograph of the tooth B before the immersion in the composition containing phytic acid according to the present invention, and FIG. 4(a) shows a photograph of the tooth B after the immersion in the composition containing phytic acid according to the present invention (Example 2), observed with electron microscope. As obvious from the photographs FIGS. 4(a) and 4(b), interprismatic spaces can be hardly observed in the photograph of FIG. 4(b) of the tooth B before the immersion, but interprismatic spaces can be observed in the photograph of FIG. 4(a) of the tooth B after the immersion to confirm the generation of vacancy in interprismatic space. The results of observations of tooth interprismatic spaces with SEM with respect to Examples and Comparative Examples are shown in Tables 2 and 4.

Test Example 7

Mouthwashes listed in Table 7 and Table 8 were prepared and the frictional feel of teeth of each of them was evaluated.

The oral cavity was rinsed with the mouthwash for 20 sec and after discharging the mouthwash, the teeth were rubbed together and the frictional feel was evaluated. The evaluation was conducted according to the following 4-scale rating, and the rating, with which the ratings of two of three examinees were identical, was adopted.

AA: No frictional feel of teeth;

A: Almost no frictional feel of teeth;

B: Good, with slight frictional feel of teeth; and

C: Obvious frictional feel of teeth.

The evaluation results are also shown in Table 7.

TABLE 7

| | Ex. 21 | Ex. 22 | Ex. 23 | Ex. 24 | Ex. 25 |
|---|---|---|---|---|---|
| Phytic acid | 0.3 | 0.3 | 0.3 | 1.0 | 0.3 |
| Glycerin | 10 | — | — | — | — |
| Sorbitol | — | 10 | — | 10 | — |
| Xylitol W | — | — | 10 | — | — |
| Erythritol | — | — | — | — | — |
| Aq. sodium hydroxide solution (48%) | Adjusted to pH 6 | Adjusted to pH 6 | Adjusted to pH 6 | Adjusted to pH 6 | Adjusted to pH 6 |
| Purified water | Balance | Balance | Balance | Balance | Balance |
| Total | 100 | 100 | 100 | 100 | 100 |
| Rating of frictional feel of teeth | C | C | C | C | C |

TABLE 8

|  | Ex. 31 | Ex. 32 | Ex. 33 | Ex. 34 | Ex. 35 | Ex. 36 | Ex. 37 | Ex. 38 | Ex. 39 | Ex. 40 |
| --- | --- | --- | --- | --- | --- | --- | --- | --- | --- | --- |
| Phytic acid | 0.3 | 0.3 | 0.3 | 1.0 | 3 | 5 | 0.5 | 0.5 | 0.5 | 0.5 |
| Glycerin | — | — | — | — | — | — | — | — | — | — |
| Sorbitol | — | — | — | — | — | — | — | — | — | — |
| Xylitol | — | — | — | — | — | — | — | — | — | — |
| Erythritol | 10 | 5 | 6 | 5 | 20 | 30 | 15 | 15 | 15 | 15 |
| Aq. sodium hydroxide solution (48%) | Adjusted to pH 6 | Adjusted to pH 6 | Adjusted to pH 6 | Adjusted to pH 6 | Adjusted to pH 6 | Adjusted to pH 6 | Adjusted to pH 6 | Adjusted to pH 7 | Adjusted to pH 8 | — |
| Aq. potassium hydroxide solution (48%) | — | — | — | — | — | — | — | — | — | Adjusted to pH 6 |
| Purified water | Balance | Balance | Balance | Balance | Balance | Balance | Balance | Balance | Balance | Balance |
| Total | 100 | 100 | 100 | 100 | 100 | 100 | 100 | 100 | 100 | 100 |
| Erythritol/Phytic acid (weight ratio) | 33.3 | 16.7 | 20 | 50 | 6.7 | 6 | 30 | 30 | 30 | 30 |
| Rating of frictional feel of tooth | AA | A | AA | AA | B | B | AA | AA | AA | AA |
| Whitening (Δb*) | −5.5 | −5.4 | −5.6 | −4.8 | −5.5 | −5.6 | −5.4 | −2.0 | −1.8 | −5.5 |
| Gloss (Δ brightness) | 7.4 | 7.0 | 7.4 | 6.8 | 7.0 | 7.4 | 7.6 | 2.5 | 2.0 | 7.6 |

As shown by Example 25 in Table 7, the mouthwash with pH 6 containing 0.3% by weight of phytic acid caused a frictional feel of teeth (C). In contrast, as shown in Table 7, with respect to the mouthwash of Example 21 containing 0.3% by weight of phytic acid and additionally glycerin, the frictional feel of teeth was not improved, but rather the frictional feel of teeth became severer. Further, with respect to Examples 22 and 23, in which sorbitol or xylitol was added at the same content as erythritol, the frictional feel of teeth was not improved. Furthermore, with respect to Example 24, in which 0.1% by weight of phytic acid and sorbitol were contained, the frictional feel of teeth was not improved. The mouthwash containing sorbitol was sweet but short of a fresh feel, and the mouthwash containing xylitol was sweet but could not render a simple fresh feel either.

In contrast thereto. Examples 31, in which erythritol was added, rendered the improving effect of the frictional feel of teeth by phytic acid. Further, as shown in Table 8, it has been made clear that, in case the erythritol/phytic acid ratio is 5 or more, the improving effect of the frictional feel of teeth is rendered, further, in case it is 15 or more, the improving effect of the frictional feel of teeth is excellent, and in case it is 20 or more, the effect on the frictional feel of teeth is more excellent. Furthermore, the sense of use with respect to the prepared mouthwash was good with an improved frictional feel of teeth and an excellent simple fresh feel.

Test Example 8

In Table 8 the result of the measurement of the change of b* as the evaluation for the whitening effect on a tooth, and the result (Δ brightness) of the measurement of the brightness as the measure for the luster or gloss of a tooth are shown. The whitening effect and the gloss of a tooth were evaluated using an extracted human tooth. For the evaluation of the whitening a human tooth was used, the crown part of the tooth was brushed in ion exchanged water for 2 min by using a toothbrush (Pyuora toothbrush, type: compact, hardness of bristle; normal; by Kao Corporation) to remove grime on the enamel surface, and for the evaluation of the gloss, a human tooth without the brushing treatment was used. For the evaluation of the whitening effect and the gloss, human teeth were immersed in the respective mouthwashes at room temperature for 48 hours, and the change (Δb*) of b* and the change (Δ brightness) of brightness between before and after the immersion were measured. Using 3 human teeth, Δb* and Δ brightness were evaluated by the respective mean values of 3 measurements.

The change (Δb*) of b* of a human tooth between before and after the immersion in each mouthwash was determined by (b* after the immersion−b* before the immersion). The b* value was determined by picking up an image with a digital camera D1x and a Ai AF Zoom Micro Nikkor ED 70-180 mm F4.5-F5.6D (both by Nikon Corporation), as well as a white flash light source (Konica Minolta Holdings, Inc.), and expressing the image by the L*a*b* color system using Adobe Photoshop CS3 (by Adobe Systems Incorporated). The closer value of b* to 0 in a positive range, means the whiter and less yellowish color, and the larger value of −Δb* (absolute value of Δb*) means the larger increase of whiteness. Among Examples 21 to 30, Example 28 and Example 29 with high pH values give small absolute values of Δb*.

The change (Δ brightness) of the brightness between before and after the immersion in the respective mouthwashes was determined by (brightness after the immersion−brightness before the immersion). The brightness was determined by a method of measuring the surface reflection intensity by image analysis using polarized light. As a device for picking up an evaluation image, an assembly of a digital single-lens reflex camera (Nikon D70); a lens of Ai AF Micro-Nikkor 105 mm F2.8D; and a stroboscopic light source of Wireless Remote Speedlight SE-R200 (all by Nikon Corporation) was used. Plastic polarizing plates (by Edmund Optics Inc,) were placed in front of the light source of Speedlight and the lens crossing the transmission axes at an angle of 30° for imaging. The average brightness of a highlight part of the picked-up image was determined by Adobe Photoshop C53 (by Adobe Systems Incorporated) The larger value of the brightness means the higher gloss, and the larger value of Δ brightness means the larger increase of the gloss.

The formulations of a mouthwash and a tooth paste according to the present invention are shown below. The evaluation of the frictional feel of tooth with respect to the mouthwash was conducted under the same conditions as Test Example 7, and the evaluations of the whiteness and the gloss were conducted under the same conditions as Test Example 8. The evaluation of frictional feel of tooth for a tooth paste was conducted on 3 examinees, by brushing with the tooth paste for 2 min followed by rinsing, and then rubbing together the teeth to rate the frictional feel. The evaluation, with which the ratings of two of three examinees were identical, was adopted. The evaluations of the whitening effect and the gloss of a tooth paste were conducted under the same condition as Test Example 8, except that a human tooth was immersed in a liquid prepared by diluting the toothpaste to 2-fold.

Example 41

Mouthwash

| Phytic acid (50% aq. solution) | 0.5 |
|---|---|
| Erythritol | 6 |
| Glycerin | 6 |
| Ethanol | 4 |
| Polyglycerin laurate | 0.5 |
| Sodium saccharin | 0.01 |
| Flavor | 0.2 |
| Aq. potassium hydroxide solution (48% aq. solution) | adjusted to pH 6 |
| Purified water | balance |
| Total | 100 (%) |

Erythritol/phytic acid 24 (weight ratio)
Rating of frictional feel of tooth AA.
Evaluation of whitening $\Delta b^* = -5.4$
Evaluation of gloss $\Delta$ brightness=7.4

Example 42

Tooth Paste

| Phytic acid (50% aq. solution) | 1 |
|---|---|
| Erythritol | 40 |
| Sorbitol solution (70% aq. solution) | 25 |
| Sodium carboxymethylcellulose | 0.8 |
| Xanthan gum | 0.1 |
| Polyethylene glycol | 5 |
| Sodium saccharin | 0.1 |
| Abrasive silica | 11 |
| Sodium lauryl sulfate | 1.5 |
| Sodium hydroxide solution (48% aq. solution) | adjusted to pH 6 |
| Flavor | 1 |
| Purified water | balance |
| Total | 100 (%) |

Erythritol/phytic acid 80 (weight ratio)
Rating of frictional feel of tooth AA
Evaluation of whitening $\Delta b^* = -5.6$
Evaluation of gloss $\Delta$ brightness=7.6

What is claimed is:

1. A method for removing a solid product formed on surfaces of teeth, the method comprising applying an oral composition to teeth, wherein the oral composition comprises 0.05 to 18% by weight of phytic acid or a salt thereof, 3 to 60% by weight erythritol, and 0-300 ppm of fluoride in terms of fluorine atom, and contains no polyvalent cation or contains a polyvalent cation in an amount of less than 0.1-fold mol relative to the phytic acid, and wherein the oral composition, as diluted with water to 30% by weight, has a pH of 5.5 to 6.5.

2. The method for removing a solid product formed on surfaces of teeth according to claim 1, wherein the oral composition further comprises an organic acid and an inorganic acid other than phytic acid in an amount of 5% by weight or less based on the phytic acid or a salt thereof.

3. The method for removing a solid product formed on surfaces of teeth according to claim 1 or 2, wherein the oral composition further comprises 5 to 60% by weight erythritol.

4. The method for removing a solid product formed on surfaces of teeth according to claim 1 or 2, wherein of the oral composition is a mouthwash and the content of erythritol is 3 to 30% by weight.

5. The method for removing a solid product formed on surfaces of teeth according to claim 1 or 2, wherein the oral composition is a tooth paste having a viscosity of 10 to 300 Pa×s at 25° C.

6. A method for imparting gloss to teeth by removing a solid product formed on surfaces of teeth, the method comprising applying an oral composition to teeth, wherein the oral composition comprises 0.05 to 18% by weight of phytic acid or a salt thereof, 3 to 60% weight erythritol, and 0-300 ppm of fluoride in terms of fluorine atom, and contains no polyvalent cation, or contains a polyvalent cation in an amount of less than 0.1-fold mol relative the phytic acid, and wherein the oral composition, as diluted with water to 30% by weight, has a pH of 5.5 to 6.5.

7. An oral composition comprising the following components (A) and (B):
 (A) phytic acid or a salt thereof in an amount of 0.01 to 10% by weight,
 (B) erythritol in an amount of 3 to 60% by weight;
 (C) 0-300 ppm of fluoride in terms of fluorine atom, and
 (D) no polyvalent cation or a polyvalent cation in an amount of less than 0.1-fold mol relative the phytic acid,
 wherein the weight ratio (B/A) of the component (B) to the component (A) is 5 to 1000, and the pH of said composition is pH 5.5-8 as diluted with water to 30% by weight.

8. The oral composition according to claim 7, wherein the oral composition, as diluted with water to 30% by weight, has a pH of 5.5 to 6.5.

9. The oral composition according to claim 7 or 8, wherein the content of (A) phytic acid or a salt thereof is 0.05 to 5% by weight.

* * * * *

UNITED STATES PATENT AND TRADEMARK OFFICE
CERTIFICATE OF CORRECTION

PATENT NO. : 8,580,234 B2
APPLICATION NO. : 13/129291
DATED : November 12, 2013
INVENTOR(S) : Isobe et al.

It is certified that error appears in the above-identified patent and that said Letters Patent is hereby corrected as shown below:

In the Specification

Examples

*Test Example 4*

Column 15
Line 49, please replace "9" with --10--.

Column 15
Line 52, please replace "10" with --11--.

*Test Example 7*

Column 19
Line 29, please replace "erythritol, the" with --erythritol in Example 31, the--.

Column 20
Line 37, please replace "21" with --31--.

Column 20
Line 37, please replace "30" with --40--.

Column 20
Line 37, please replace "28" with --38--.

Column 20
Line 37, please replace "29" with --39--.

Signed and Sealed this
Eleventh Day of March, 2014

Michelle K. Lee
*Deputy Director of the United States Patent and Trademark Office*